United States Patent [19]

Rosenberg et al.

[11] Patent Number: 6,030,940
[45] Date of Patent: *Feb. 29, 2000

[54] PEPTIDE ANALOG INHIBITORS OF UROKINASE RECEPTOR ACTIVITY

[75] Inventors: Steven Rosenberg; Kerry L. Spear, both of Oakland, Calif.; Robert Valerio, Cranbourne; Andrew Bray, Boronia, both of Australia

[73] Assignee: Chiron Corporation, Emeryville, Calif.

[*] Notice: This patent is subject to a terminal disclaimer.

[21] Appl. No.: 08/800,213

[22] Filed: Feb. 12, 1997

Related U.S. Application Data

[63] Continuation-in-part of application No. PCT/US96/12044, Jul. 19, 1996, and a continuation-in-part of application No. 08/509,208, Jul. 31, 1995.

[51] Int. Cl.[7] .......................... A61K 38/04; A61K 38/10; C07K 7/00
[52] U.S. Cl. ................... 514/2; 514/15; 530/300; 530/327
[58] Field of Search ...................... 530/350, 300, 530/327; 514/2, 15

[56] References Cited

U.S. PATENT DOCUMENTS

| | | | |
|---|---|---|---|
| 5,340,833 | 8/1994 | Bridges et al. | 514/443 |
| 5,656,726 | 8/1997 | Rosenberg et al. | 530/326 |

*Primary Examiner*—Paula K. Hutzell
*Assistant Examiner*—Michael Pak
*Attorney, Agent, or Firm*—Bret Field; David P. Lentini; Robert P. Blackburn

[57] ABSTRACT

Effective urokinase-type plasminogen activator receptor antagonists have sequences selected from the group LNFGQYLWYT, LCFGCYLWYT, LNFGCYLWCT, LNFGQYLnAYT, LNFdSQYLWYT, LCFGCYLWY, LNFdSQYLnAYT, LNFGdCYLWCT, LCFdSCYLWYT, LCFdSCYLnAYT, LNFdSCYLWCT, or active analogs or active portions thereof.

6 Claims, No Drawings

PEPTIDE ANALOG INHIBITORS OF UROKINASE RECEPTOR ACTIVITY

This application is a continuation-in-part of International Application No. PCT/US96/12044, filed Jul. 19, 1996 and continuation-in-part of U.S. patent application Ser. No. 08/509,208 filed Jul. 31, 1995.

DESCRIPTION

1. Technical Field

This invention relates to the fields of cellular biology and protein expression. More particularly, the invention relates to peptide and peptide analog ligands of the urokinase plasminogen activator receptor, and methods for preparing the same.

2. Background of the Invention

Urokinase-type plasminogen activator (uPA) is a multi-domain serine pro-tease, having a catalytic "B" chain (amino acids 144–411), and an amino-terminal fragment ("ATF", aa 1–143) consisting of a growth factor-like domain (4–43) and a kringle (aa 47–135). The uPA kringle appears to bind heparin, but not fibrin, lysine, or aminohexanoic acid. The growth factor-like domain bears some similarity to the structure of epidermal growth factor (EGF), and is thus also referred to as an "EGF-like" domain. The single chain pro-uPA is activated by plasmin, cleaving the chain into the two chain active form, which is linked together by a disulfide bond.

uPA binds to its specific cell surface receptor (uPAR). The binding inter-action is apparently mediated by the EGF-like domain (S. A. Rabbani et al., *J Biol Chem* (1992) 267:14151–56). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including $a_2$ antiplasmin, PAI-1 and PAI-2.

Plasmin can activate or degrade extracellular proteins such as fibrinogen, fibronectin, and zymogens. Plasminogen activators thus can regulate extracellular proteolysis, fibrin clot lysis, tissue remodeling, developmental cell migration, inflammation, and metastasis. Accordingly, there is great interest in developing uPA inhibitors and uPA receptor antagonists. E. Appella et al., *J Biol Chem* (1987) 262:4437–40, determined that receptor binding activity is localized in the EGF-like domain, and that residues 12–32 appear to be critical for binding. The critical domain alone ($uPA_{12-32}$) bound uPAR with an affinity of 40 nM (about 100 fold less than intact ATF).

S. A. Rabbani et al., supra, disclosed that the EGF-like domain is fucosylated at $Thr_{18}$, and reported that fucosylated EGF-like domain ($uPA_{4-43}$, produced by cleavage from pro-uPA) was mitogenic for an osteosarcoma cell line, SaOS-2. In contrast, non-fucosylated EGF-like domain bound UPAR with an affinity equal to the fucosylated EGF-like domain, but exhibited no mitogenic activity. Non-fucosylated EGF-like domain competed for binding to uPAR with fucosylated EGF-like domain, and reduced the mitogenic activity observed. Neither fucosylated nor non-fucosylated EGF-like domain was mitogenic in U937 fibroblast cells.

R. J. Goodson et al., *Proc Natl Acad Sci USA* (1994) 91:7129–33 disclosed a number of peptide sequences which bind to the human uPA receptor with micromolar affinities.

DISCLOSURE OF THE INVENTION

One aspect of the invention is the set of polypeptides disclosed herein, and analogs thereof, which bind to the urokinase plasminogen activator receptor and inhibit the receptor binding activity of urokinase-type plasminogen activator.

Another aspect of the invention is a method for treating a urokinase-modulated disorder, such as cancer and metastasis, by administering an effective amount of a peptide of the invention or an analog thereof.

Another aspect of the invention is a composition suitable for treating a urokinase-modulated disorder, comprising an effective amount of a peptide of the invention or an analog thereof in combination with a pharmaceutically acceptable excipient.

MODES OF CARRYING OUT THE INVENTION

A. Definitions

The term "huPA" refers specifically to human urokinase-type plasminogen activator. The "EGF-like domain" is that portion of the huPA molecule responsible for mediating huPA binding to its receptor (uPAR). The EGF-like domain, sometimes called the growth factor-like domain ("GFD"), is located within the first 48 residues of huPA. The critical residues (essential for binding activity) have been localized to positions 12–32, although a peptide containing only those residues does not exhibit a binding affinity high enough to serve as a useful receptor antagonist.

"Peptides of the invention" and "huPAR antagonist peptides" have one of the following sequences:

LNFGQYLWYT (SEQ ID NO: 1),
LCFGCYLWYT (SEQ ID NO: 2),
LNFGCYLWCT (SEQ ID NO: 3),
LNFGQYLnAYT (SEQ ID NO: 4),
LNFdSQYLWYT (SEQ ID NO: 5),
LCFGCYLWY (SEQ ID NO: 6),
LNFdSQYLnAYT (SEQ ID NO: 7),
LNFGdCYLWCT (SEQ ID NO: 8),
LCFdSCYLWYT (SEQ ID NO: 9),
LCFdSCYLnAYT (SEQ ID NO: 10),
LNFdSCYLWCT (SEQ ID NO: 11), where dS denotes D-Ser, dC denotes D-Cys, and nA denotes 1-naphthylalanine.

The term "active analog" refers to a polypeptide differing from the sequence of one of the peptides of the invention, or an active portion thereof by 1–3 amino acids, but which still exhibits a $K_d \leq 250$ nM with huPAR. The differences are preferably conservative amino acid substitutions, in which an amino acid is replaced with another amino acid or amino acid analog of similar character. For example, the following substitutions are considered "conservative" of natural amino acids: Gly⇔Ala; Val⇔Ile⇔Leu; Asp⇔Glu; Lys⇔Arg; Asn⇔Gln; and Phe⇔Trp⇔Tyr. Conservative analog substitutions include substitution of D-isomers for L-isomers, phenylglycine for phenylalanine, 1-naphthylalanine for tryptophan, and the like. Nonconservative changes are generally substitutions of one of the above amino acids with an amino acid from a different group (e.g., substituting Asn for Glu), or substituting Cys, Met, His, or Pro for any of the above amino acids.

The term "fusion protein" refers to a protein of the form:

$$X_1\text{-(peptide)}_n\text{-}X_2$$

in which at least one of $X_1$ and $X_2$ is a protein or polypeptide, (peptide) is a peptide of the invention or an active analog thereof, and n is an integer from 1 to 100. $X_1$ and $X_2$ may be the same or different, and may be portions of the same protein (e.g., the peptide may be inserted at an internal position within the primary sequence of another protein). $X_1$ and $X_2$ may be selected to improve expression of the peptide/fusion protein, to enhance purification, and/or to provide a biological activity. The peptides of the invention may be the same or different, and may be separated by peptide spacers (e.g., if it is desired to prepare a fusion protein capable of crosslinking huPAR on the cell surface). Alternatively, the peptides may be separated by proteolytic cleavage sites, to facilitate cleavage of the fusion protein into individual active peptides.

The term "conventional amino acid" refers to the amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine The term "nonconventional amino acid" refers to amino acids other than conventional amino acids. Presently preferred nonconventional amino acids are:

| | |
|---|---|
| Nle = L-norleucine; | Aabu = α-aminobutyric acid; |
| Hphe = L-homophenylalanine; | Nva = L-norvaline; |
| Gabu = γ-aminobutyric acid; | Dala = D-alanine; |
| Dcys = D-cysteine; | Dasp = D-aspartic acid; |
| Dglu = D-glutamic acid; | Dphe = D-phenylalanine; |
| Dhis = D-histidine; | Dile = D-isoleucine; |
| Dlys = D-lysine; | Dleu = D-leucine; |
| Dmet = D-methionine; | Dasn = D-asparagine; |
| Dpro = D-proline; | Dgln = D-glutamine; |
| Darg = D-arginine; | Dser = D-serine; |
| Dthr = D-threonine; | Dval = D-valine; |
| Dtrp = D-tryptophan; | Dtyr = D-tyrosine; |
| Dorn = D-ornithine; | Aib = aminoisobutyric acid; |
| Etg = L-ethylglycine; | Tbug = L-t-butylglycine; |
| Pen = penicillamine; | Anap = I-naphthylalanine; |
| Chexa = cyclohexylalanine; | Cpen = cyclopentylalanine; |
| Cpro = aminocyclopropane carboxylate; | Norb = aminonorbornylcarboxylate; |
| Mala = L-α-methylalanine; | Mcys = L-α-methylcysteine; |
| Masp = L-α-methylaspartic acid; | Mglu = L-α-methylglutamic acid; |
| Mphe = L-α-methylphenylalanine; | Mhis = Lα-methylhistidine; |
| Mile = L-α-methylisoleucine; | Mlys = L-α-methyllysine; |
| Mleu = L-α-methylleucine; | Mmet = L-α-methylmethionine; |
| Masn = L-α-methylasparagine; | Mpro = L-α-methylproline; |
| Mgln = L-α-methylglutamine; | Marg = L-α-methylarginine; |
| Mser = L-a-methylserine; | Mthr = L-α-methylthreonine; |
| Mval = L-a-methylvaline; | Mtrp = L-α-methyltryptophan; |
| Mtyr = L-a-methyltyrosine; | Morn = L-α-methylornithine; |
| Mnle = L-a-methylnorleucine; | Maabu = α-amino-α-methylbutyric acid; |
| Mnva = L-a-methylnorvaiine; | Mhphe = L-α-methylhomophenylalanine; |
| Metg = L-a-methylethylglycine; | Mgabu = α-methyl-γ-aminobutyric acid; |
| Maib = α-methylaminoisobutyric acid; | Mtbug = L-α-methyl-t-butylglycine; |
| Mpen = α-methylpenicillamine; | Manap = α-methyl-α-naphthylalanine; |
| Mchexa = α-methylcyclohexylalanine; | Mcpen = α-methylcyclopentylalanine; |
| Dmala = D-α-methylalanine; | Dmorn = D-α-methylornithine; |
| Dmcys = D-α-methylcysteine; | Dmasp = D-α-methylaspartic acid; |
| Dmglu = D-α-methylglutamic acid; | Dmphe = D-α-methylphenylalanine; |
| Dmhis = D-α-methylhistidine; | Dmile = D-α-methylisoleucine; |
| Dmlys = D-α-methyllysine; | Dmleu = D-α-methylleucine; |
| Dmmet = D-α-methylmethionine; | Dmasn = D-α-methylasparagine; |
| Dmpro = D-α-methylproline; | Dmgln = D-α-methylglutamine; |
| Dmarg = D-α-methylarginine; | Dmser = D-α-methylserine; |
| Dmthr = D-α-methylthreopine; | Dmvai = D-α-methylvaline; |
| Dmtrp = D-α-methyltryptophan; | Dmtyr = D-α-methyltyrosine; |
| Nmala = L-N-methylalanine; | Nmcys = L-N-methylcysteine; |
| Nmasp = L-N-methylaspartic acid; | Nmglu = L-N-methylglutamic acid; |
| Nmphe = L-N-methylphenylalanine; | Nmhis = L-N-methylhistidine; |
| Nmile = L-N-methylisoleucine; | Nmlys = L-N-methyllysine; |
| Nmleu = L-N-methylleucine; | Nmmet = L-N-methylmethionine; |
| Nmasn = L-N-methylasparagine; | Nmchexa = N-methylcyclohexylalanine; |
| Nmgln = L-N-methylglutamine; | Nmarg = L-N-methylarginine; |
| Nmser = L-N-methylserine; | Nmthr = L-N-methylthreonine; |
| Nmval = L-N-methylvaline; | Nmtrp = L-N-methyltryptophan; |
| Nmtyr = L-N-methyltyrosine; | Nmorn = L-N-methylornithine; |
| Nmnle = L-N-methylnorleucine; | Nmaabu = N-amino-α-methylbutyric acid; |
| Nmnva = L-N-methylnorvaline; methylhomophenylalanine; | Nmhphe = L-N- |
| Nmetg = L-N-methylethylglycine; | Nmgabu = N-methyl-γ-aminobutyric acid; |
| Nmcpen = N-methylcyclopentylalanine; | Nmtbug = L-N-methyl-t-butylglycine; |
| Nmpen = N-methylpenicillamine; | Nmanap = N-methyl-α-naphthylalanine; |
| Nmaib = N-methylaminoisobutyric acid; | Naeg = N-(2-aminoethyl)glycine; |
| Dnmala = D-N-methylalanine; | Dnmorn = D-N-methylornithine; |
| Dnmcys = D-N-methylcysteine; | Dnmasp = D-N-methylaspartic acid; |
| Dnmglu = D-N-methylglutamic acid; | Dnmphe = D-N-methylphenylalanine; |
| Dnmhis = D-N-methylhistidine; | Dnmile = D-N-methylisoleucine; |

-continued

| | |
|---|---|
| Dnmlys = D-N-methyllysine; | Dnmleu = D-N-methylleucine; |
| Dnmmet = D-N-methylmethionine; | Dnmasn = D-N-methylasparagine; |
| Dnmpro = D-N-methylproline; | Dnmgln = D-N-methylglutamine; |
| Dnmarg = D-N-methylarginine; | Dnmser = D-N-methylserine; |
| Dnmthr = D-N-methylthreonine; | Dnmval = D-N-methylvaline; |
| Dnmtrp = D-N-methyltryptophan; | Dnmtyr = D-N-methyltyrosine; |
| Nala = N-methylglycine (sarcosine); | Nasp = N-(carboxymethyl)glycine; |
| Nglu = N-(2-carboxyethyl)glycine; | Nphe = N-benzylglycine; |
| Nhhis = N-(imidazolylethyl)glycine; | Nile = N-(1-methylpropyl)glycine; |
| Nlys = N-(4-aminobutyl)glycine; | Nleu = N-(2-methylpropyl)glycine; |
| Nmet = N-(2-methylthioethyl)glycine; | Nhser = N-(hydroxyethyl)glycine; |
| Nasn = N-(carbamylmethyl)glycine; | Ngln = N-(2-carbamylethyl)glycine; |
| Nval = N-(1-methylethyl)glycine; | Narg = N-(3-guanidinopropyl)glycine; |
| Nhtrp = N-(3-indolylethyl)glycine; | Nhtyr = N-(p-hydroxyphenethyl)glycine; |
| Nthr = N-(1-hydroxyethyl)glycine; | Ncys = N-(thiomethyl)glycine; and |
| Norn = N-(3-aminopropyl)glycine; | Ncpro = N-cyclopropylglycine; |
| Ncbut = N-cyclobutyglycine; | Nchex = N-cyclohexylglycine; |
| Nchep = N-cycloheptylglycine; | Ncoct = N-cyclooctylglycine; |
| Ncdec = N-cyclodecylglycine; | Ncund = N-cycloundecylglycine; |
| Ncdod = N-cyclododecylglycine; | Nbhm = N-(2,2-diphenylethyl)glycine; |
| Nbhe = N-(3,3-diphenylpropyl)glycine; | |
| Nnbhm = N-(N-(2,2-diphenylethyl)carbamylmethyl)glycine; | |
| Nnbhe = N-(N-(3,3-diphenylpropyl)carbamylmethyl)glycine; and | |
| Nbmc = 1-carboxy-1-(2,2-diphenylethylamino)cyclopropane. | |

The term "expression vector" refers to an oligonucleotide which encodes the huPAR antagonist polypeptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Expression vectors may further comprise an oligonucleotide encoding a signal leader polypeptide. When "operatively connected", the huPAR antagonist is expressed downstream and in frame with the signal leader, which then provides for secretion of the huPAR antagonist polypeptide by the host to the extracellular medium. The presently preferred signal leader is the *Saccharomyces cerevisiae* a-factor leader (particularly when modified to delete extraneous Glu—Ala sequences).

The term "transcriptional promoter" refers to an oligonucleotide sequence which provides for regulation of the DNA→mRNA transcription process, typically based on temperature, or the presence or absence of metabolites, inhibitors, or inducers. Transcriptional promoters may be regulated (inducible/repressible) or constitutive. Yeast glycolytic enzyme promoters are capable of driving the transcription and expression of heterologous proteins to high levels, and are particularly preferred. The presently preferred promoter is the hybrid ADH2/GAP promoter described in Tekamp-Olson et al., U.S. Pat. No. 4,876,197 (incorporated herein by reference), comprising the *S. cerevisiae* glyceraldehyde-3-phosphate dehydrogenase promoter in combination with the *S. cerevisiae* alcohol dehydrogenase II upstream activation site.

The term "host" refers to a yeast cell suitable for expressing heterologous polypeptides. There are a variety of suitable genera, such as Saccharomyces, Schizosaccharomyces, Kluveromyces, Pichia, Hansenula, and the like. Presently preferred are yeast of the Saccharomyces genus, particularly *Saccharomyces cerevisiae*.

The term "huPA-mediated disorder" refers to a disease state or malady which is caused or exacerbated by a biological activity of huPA. The primary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated ATF or EGF-like domain are also mitogenic for tumor cells, which sometimes self-activate in an autocrine mechanism. Accordingly, the huPAR antagonist of the invention is effective in inhibiting the proliferation of huPA-activated tumor cells.

The term "effective amount" refers to an amount of huPAR antagonist polypeptide sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

B. General Method

The peptides of the invention may be synthesized by standard chemical methods, such as solid phase peptide synthesis. Alternatively, if desired, the peptides composed of naturally-occurring amino acids may be expressed in an appropriate host, preferably as part of a fusion protein. Peptides prepared as part of a fusion protein are preferably expressed in a host cell. Presently preferred hosts are yeasts, particularly Saccharomyces, Schizosaccharomyces, Kluveromyces, Pichia, Hansenula, and the like, especially *S. cerevisiae*. Strains MB2-1 and AB110 are presently preferred, as are strains JSC302 and JSC308 (for fusion protein constructs).

The expression vector is constructed according to known methods, and typically comprises a plasmid functional in the selected host. The oligonucleotide encoding the peptide or fusion protein will generally be synthesized chemically, or cloned from a suitable source (e.g., from a bacteriophage library). Stable plasmids generally require an origin of replication (such as the yeast $2\mu$ ori), and one or more selectable markers (such as antibiotic resistance) which can be used to screen for transformants and force retention of the plasmid. The vector should provide a promoter which is functional in the selected host cell, preferably a promoter derived from yeast glycolytic enzyme promoters such as GAPDH, GAL, and ADH2. These promoters are highly efficient, and can be used to drive expression of heterologous proteins up to about 10% of the host cell weight. The presently preferred promoter is a hybrid ADH2/GAP promoter comprising the *S. cerevisiae* glyceraldehyde-3-phosphate dehydrogenase promoter in combination with the *S. cerevisiae* alcohol dehydrogenase II upstream activation site.

The expression vector should ideally provide a signal leader sequence between the promoter and the huPAR antagonist polypeptide sequence. The signal leader sequence provides for translocation of the huPAR antagonist polypeptide through the endoplasmic reticulum and export from the cell into the extracellular medium, where it may be easily harvested. There are a number of signal leader sequences known that are functional in yeast. Presently preferred are the yeast oc-factor leader (see U.S. Pat. No. 4,751,180, incorporated herein by reference).

Alternatively, the vector may provide for integration into the host genome, as is described by Shuster, PCT W092101800, incorporated herein by reference.

Transformations into yeast can be carried out according to the method of A. Hinnen et al., *Proc Natl Acad Sci USA* (1978) 75:1929–33, or H. Ito et al., *J Bacteriol* (1983) 153:163–68. After DNA is taken up by the host cell, the vector integrates into the yeast genome at one or more sites homologous to its targeting sequence. It is presently preferred to linearize the vector by cleaving it within the targeting sequence using a restriction endonuclease, as this procedure increases the efficiency of integration.

Following successful transformations, the number of integrated sequences may be increased by classical genetic techniques. As the individual cell clones can carry integrated vectors at different locations, a genetic cross between two appropriate strains followed by sporulation and recovery of segregants can result in a new yeast strain having the integrated sequences of both original parent strains. Continued cycles of this method with other integratively transformed strains can be used to further increase the copies of integrated plasmids in a yeast host strain. One may also amplify the integrated sequences by standard techniques, for example by treating the cells with increasing concentrations of copper ions (where a gene for copper resistance has been included in the integrating vector).

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al., *Proc Natl Acad Sci USA* (1969) 62:1159, optionally following chloramphenicol amplification (D. B. Clewell, J *Bacteriol* (1972) 110:667). Isolated DNA is analyzed by restriction mapping and/or sequenced by the dideoxy method of F. Sanger et al., *Proc Natl Acad Sci USA* (1977) 74:5463 as further described by Messing et al., *Nucl Acids Res* (1981) 9:309, or by the method of Maxam and Gilbert, *Meth Enzymol* (1980) 65:499.

Fusion proteins may be prepared by the methods described above. One may improve expression of peptides by expressing them as fusion proteins with a well-expressed protein leader or fusion partner. For example, Cu/Zn superoxide dismutase (SOD) is highly-expressed in yeast when used as a fusion protein leader. See Cousens et al., U.S. Pat. No. 4,751,180, incorporated herein by reference in full. Other suitable fusion partners include β-galactosidase, human IgG antibody fragments (e.g., Fc fragments), ubiquitin, and the like. Additionally, one may include secretion leaders, such as the yeast α-factor leader or bacterial OmpA leader, to direct secretion of the fusion protein to the extracellular medium. One may also employ fusion partners which will impart a biological activity to the fusion protein. For example, one may use a cytotoxic protein such as ricin in order to kill cells bearing huPAR.

huPAR antagonist polypeptides, active portions, active analogs, active peptoid analogs, and fusion proteins (collectively "antagonists") may be assayed for activity by methods known in the art. For example, the methods provided in the examples below, and in R. J. Goodson et al., *Proc Natl Acad Sci USA* (1994) 91:7129–33 are suitable. Additionally, active analogs may be screened conveniently and efficiently by following the method of H. M. Geysen et al., U.S. Pat. No. 4,708,871. Geysen described a method for synthesizing a set of overlapping oligopeptides derived from any selected protein (e.g., $aa_1$–$aa_7$, $aa_2$–$aa_8$, $aa_3$–$aa_9$, etc.) bound to a solid phase array of pins, with a unique oligopeptide on each pin. The pins are arranged to match the format of a 96-well microtiter plate, permitting one to assay all pins simultaneously, e.g., for binding to a labeled ligand. Using this method, one may readily determine the binding affinity for the ligand for every possible subset of consecutive conventional and/or nonconventional amino acids presented in any selected antagonist. One may assay competition of the antagonist against native huPA for cell surface receptor binding. Competition for the receptor correlates with inhibition of huPA biological activity. One may assay huPAR antagonists for anti-mitogenic activity on appropriate tumor cell lines, such as the osteosarcoma cell line SaOS-2 described in the art. Inhibition of mitogenic activity may be determined by comparing the uptake of $^3$H-T in osteosarcoma cells treated with the antagonist against controls. One may also assay huPAR antagonists for anti-invasive activity on appropriate tumor cell lines, such as HOC-1 and HCT116 (W. Schlechte et al, *Cancer Comm* (1990) 2:173–79; H. Kobayashi et al., *Brit J Cancer* (1993) 67:537–44).

huPAR antagonists are administered orally, topically, or by parenteral means, including subcutaneous and intramuscular injection, implantation of sustained release depots, intravenous injection, intranasal administration, and the like. When used to treat tumors, it may be advantageous to apply the huPAR antagonist peptide directly to the site, e.g., during surgery to remove the bulk of the tumor. Accordingly, huPAR antagonists may be administered as a pharmaceutical composition comprising a huPAR antagonist in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable pre=servatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively, one may incorporate or encapsulate the huPAR antagonist in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dohme), Lacrilube®, and the like, or may employ topical preparations such as that described in U.S. Pat. No. 5,124,155, incorporated herein by reference. Further, one may provide a huPAR antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remincton's Pharmaceutical Sciences* (Mack Pub. Co.).

The amount of huPAR antagonist required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 0.010 mg/Kg to about 500 mg/Kg huPAR antagonist administered i.v. or subcutaneously is effective for inhibiting tissue damage due to chronic inflammation. For treating corneal angiogenesis, huPAR antagonist may be administered locally in a gel or matrix at a concentration of about 0.01 mg/Kg to about 50 mg/Kg.

C. Examples

The examples presented below are provided as a further guide to the practitioner of ordinary skill in the art, and are not to be construed as limiting the invention in any way.

EXAMPLE 1

(Peptide Synthesis)

The following peptides were synthesized using the "pin method" and supplied by Chiron Mimotopes (Melbourne, Australia):

LNFGQYLWYT (SEQ ID NO: 1),
LCFGCYLWYT (SEQ ID NO: 2),
LNFGCYLWCT (SEQ ID NO: 3),
LNFGQYLnAYT (SEQ ID NO: 4),
LNFdSQYLWYT (SEQ ID NO: 5),
LCFGCYLWY (SEQ ID NO: 6),
LNFdSQYLnAYT (SEQ ID NO: 7),
LNFGdCYLWCT (SEQ ID NO: 8),
LCFdSCYLWYT (SEQ ID NO: 9),
LCFdSCYLnAYT (SEQ ID NO: 10),
LNFdSCYLWCT (SEQ ID NO: 11), where dS denotes D-Ser, dC denotes D-Cys, and nA denotes 1-naphthylalanine. All peptides were purified by preparative reverse phase HPLC and concentrations determined by amino acid analysis.

EXAMPLE 2

(Activity Assay)

Purified soluble uPAR was biotinylated with NHS-biotin (Molecular Probes) and immobilized at 0.3 Tg/mL in phosphate-buffered saline (PBS)/0.1% BSA on streptavidin-coated Immulon-2 96-well Removawell plates. Human uPA N-terminal fragment (ATF; from M. Shuman, University of California, San Francisco) was iodinated by the Iodo-Gen method (Pierce). Unincorporated $^{125}$I was separated from labeled protein by Sephadex G-25 chromatography. The specific activity of the labeled protein was between $5\times10^5$ and $1\times10^6$ dpm/mol. The iodinated tracer (100–500 pM) was incubated with the peptides prepared in Example 1 triplicate for 2h at room temperature in PBS/0.1% BSA in a total volume of 200 TL. The plates were washed with PBS/0.1% BSA 3X, and remaining bound radioactivity was measured on an LKB 1277 Gammamaster. Scatchard analysis was performed by using the LIGAND program (Biosoft, Milltown, N.J.).

The results were as follows:

| Seq ID. | Sequence | $IC_{50}$ (nM) |
| --- | --- | --- |
| 1 | LNFGQYLWYT | 41 ± 17 |
| 2 | LCFGCYLWYT | 35 ± 9 |
| 3 | LNFGCYLWCT | 17 ± 1 |
| 4 | LNFGQYLnAYT | 7 ± 1.2 |
| 4 | LNFGQYLnAYT | 6 ± 1 |
| 5 | LNFdSQYLWYT | 7 ± 3 |
| 5 | LNFdSQYLWYT | 11 ± 3 |
| 5 | LNFdSQYLWYT | 11 ± 2.6 |
| 6 | LCFGCYLWY | 240 ± 37 |
| 7 | LNFdSQYLnAYT | 33 ± 3 |
| 8 | LNFGdCYLWCT | 8 ± 1 |
| 8 | LNFGdCYLWCT | 14 ± 1.5 |
| 9 | LCFdSCYLWYT | 9 ± 1.8 |
| 9 | LCFdSCYLWYT | 23 ± 2.9 |
| 10 | LCFdSCYLnAYT | 79 ± 10 |
| 11 | LNFdSCYLWCT | 225 ± 40 |

EXAMPLE 3

(Formulation of huPA Antagonists)

huPA antagonist formulations suitable for use in chemotherapy are prepared as follows:

| A) Injectable Formulation: | |
| --- | --- |
| LNFGQYLnAYT (SEQ ID NO:4) | 25.0 mg |
| $Na_2HPO_4$ (0.5 M) | 0.5 mL |
| mannitol (25%) | 2.5 mL |
| sodium laureate (1%) | 2.5 mL |
| pH | 7.5 |
| PBS qs | 20.0 mL |

This formulation is prepared following the procedure set forth in U.S. Pat. No. 4,816,440, incorporated herein by reference. The formulation is administered by parenteral injection at the site to be treated. The formulation is also generally suitable for administration as eyedrops directly to the conjunctiva, or by intranasal administration as an aerosol. Alternatively, a concentrated formulation (e.g., reducing the phosphate buffered saline to 2 mL) may be used to fill an Alzet® minipump, and the minipump implanted at the site to be treated.

| B) Ophthalmic Preparation: | |
|---|---|
| LNFGQYLnAYT (SEQ ID NO:4) | 1.0 mg |
| fibronectin | 69.0 mg |
| albumin | 37.5 mg |
| water qs | 3.0 mL |
| HCl (0.01 M) qs | pH 4.0 |

This dosage form is prepared following the procedure set forth in U.S. Pat. No. 5,124,155, incorporated herein by reference. The fibronectin and albumin are dissolved in water to form a 3.0 mL solution, and HCl added to a pH of 4.0, causing the fibronectin to flocculate. The flocculent is filtered, and combined with the peptide. The mixture is then placed in a contact lens mold, and the mold closed for 30 min to form a corneal "shield" in the shape of a contact lens. The shield releases peptide over a period of time, and is useful for preventing angiogenesis of corneal tissue following ophthalmic surgery.

The present invention has been described with reference to specific embodiments. However, this application is intended to cover those changes and substitutions which may be made by those skilled in the art without departing from the spirit and the scope of the appended claims.

What is claimed is:

1. A linear 9 to 11 mer peptide selected from the group consisting of:

LNFGQYLWYT (SEQ ID NO: 1),
LCFGCYLWYT (SEQ ID NO: 2),
LNFGCYLWCT (SEQ ID NO: 3),
LNFGQYLnAYT (SEQ ID NO: 4),
LNFdSQYLWYT (SEQ ID NO: 5),
LCFGCYLWY (SEQ ID NO: 6),
LNFdSQYLnAYT (SEQ ID NO: 7),
LNFGdCYLWCT (SEQ ID NO: 8),
LCFdSCYLWYT (SEQ ID NO: 9),
LCFdSCYLnAYT (SEQ ID NO: 10),
LNFdSCYLWCT (SEQ ID NO: 11), or an active 9 to 11 mer analog thereof, wherein the sequence of said active analog differs from the sequence of said peptide by 1 to 3 amino acid residues, and wherein said active analog exhibits a $K_d \leq 250$ nM with huPAR.

2. A method for treating huPA-mediated disorders, said method comprising: administering to a subject an effective amount of a linear 9–11 mer peptide selected from the group consisting of:

LNFGQYLWYT (SEQ ID NO: 1),
LCFGCYLWYT (SEQ ID NO: 2),
LNFGCYLWCT (SEQ ID NO: 3),
LNFGQYLnAYT (SEQ ID NO: 4),
LNFdSQYLWYT (SEQ ID NO: 5),
LCFGCYLWY (SEQ ID NO: 6),
LNFdSQYLnAYT (SEQ ID NO: 7),
LNFGdCYLWCT (SEQ ID NO: 8),
LCFdSCYLWYT (SEQ ID NO: 9),
LCFdSCYLnAYT (SEQ ID NO: 10),
LNFdSCYLWCT (SEQ ID NO: 11), or an active 9 to 11 mer analog thereof, wherein the sequence of said active analog differs from the sequence of said peptide by 1 to 3 amino acid residues, and wherein said active analog exhibits a $K_d \leq 250$ nM with huPAR.

3. The method of claim 2, wherein said huPA-mediated disorder is selected from the group consisting of metastasis, inappropriate angiogenesis, and chronic inflammation.

4. The method of claim 2, wherein said huPA-mediated disorder is selected from the group consisting of Kaposi's sarcoma, diabetic retinopathy, and rheumatoid arthritis.

5. The method of claim 2, wherein said peptide is administered by instillation in the eye.

6. A composition comprising:

a pharmaceutically acceptable excipient, and
an effective amount of a linear 9–11 mer peptide selected from the group consisting of:

LNFGQYLWYT (SEQ ID NO: 1),
LCFGCYLWYT (SEQ ID NO: 2),
LNFGCYLWCT (SEQ ID NO: 3),
LNFGQYLnAYT (SEQ ID NO: 4),
LNFdSQYLWYT (SEQ ID NO: 5),
LCFGCYLWY (SEQ ID NO: 6),
LNFdSQYLnAYT (SEQ ID NO: 7),
LNFGdCYLWCT (SEQ ID NO: 8),
LCFdSCYLWYT (SEQ ID NO: 9),
LCFdSCYLnAYT (SEQ ID NO: 10),
LNFdSCYLWCT (SEQ ID NO: 11), or an active 9 to 11 mer analog thereof, wherein the sequence of said active analog differs from the sequence of said peptide by 1 to 3 amino acid residues, and wherein said active analog exhibits a $K_d \leq 250$ nM with huPAR.

* * * * *

```
                        SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Leu Asn Phe Gly Gln Tyr Leu Trp Tyr Thr
   1               5                   10

(2) INFORMATION FOR SEQ ID NO:2:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

Leu Cys Phe Gly Cys Tyr Leu Trp Tyr Thr
   1               5                   10

(2) INFORMATION FOR SEQ ID NO:3:

(i) SEQUENCE CHARACTERISTICS:
             (A) LENGTH: 10 amino acids
             (B) TYPE: amino acid
             (C) STRANDEDNESS: single
             (D) TOPOLOGY: linear
```

```
    (ii) MOLECULE TYPE: peptide (iii) HYPOTHETICAL: NO (iv) ANTI-SENSE: NO (xi) SEQUENCE DESCRIPTION: SEQ ID NO:3:

Leu Asn Phe Gly Cys Tyr Leu Trp Cys Thr
1               5                   10

(2) INFORMATION FOR SEQ ID NO:4:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 8
         (D) OTHER INFORMATION: /product= "OTHER"
             /label= Xaa
             /note= "1-naphthylalanine"

(xi) SEQUENCE DESCRIPTION: SEQ ID NO:4:

Leu Asn Phe Gly Gln Tyr Leu Xaa Tyr Thr
1               5                   10

(2) INFORMATION FOR SEQ ID NO:5:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 4
         (D) OTHER INFORMATION: /product= "OTHER"
             /label= Xaa
             /note= "d-serine"

(xi) SEQUENCE DESCRIPTION: SEQ ID NO:5:

Leu Asn Phe Xaa Gln Tyr Leu Trp Tyr Thr
1               5                   10

(2) INFORMATION FOR SEQ ID NO:6:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (iii) HYPOTHETICAL: NO
```

(iv) ANTI-SENSE: NO (xi) SEQUENCE DESCRIPTION: SEQ ID NO:6:

Leu Cys Phe Gly Cys Tyr Leu Trp Tyr
1               5

(2) INFORMATION FOR SEQ ID NO:7:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 4
            (D) OTHER INFORMATION: /product= "OTHER"
                /label= Xaa
                /note= "d-serine"

(ix) FEATURE:
            (A) NAME/KEY: Modified-site
            (B) LOCATION: 8
            (D) OTHER INFORMATION: /product= "OTHER"
                /label= Xaa
                /note= "1-naphthylalanine"

(xi) SEQUENCE DESCRIPTION: SEQ ID NO:7:

Leu Asn Phe Xaa Gln Tyr Leu Xaa Tyr Thr
1               5                   10

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 5
            (D) OTHER INFORMATION: /product= "OTHER"
                /label= Xaa
                /note= "d-cysteine"

(xi) SEQUENCE DESCRIPTION: SEQ ID NO:8:

Leu Asn Phe Gly Xaa Tyr Leu Trp Cys Thr
1               5                   10

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide

```
    (iii) HYPOTHETICAL: NO (iv) ANTI-SENSE: NO (ix) FEATURE:
         (A) NAME/KEY: Modified-site
         (B) LOCATION: 4
         (D) OTHER INFORMATION: /product= "OTHER"
             /label= Xaa
             /note= "d-serine"

(xi) SEQUENCE DESCRIPTION: SEQ ID NO:9:

Leu Cys Phe Xaa Cys Tyr Leu Trp Tyr Thr
1               5                   10

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 4
         (D) OTHER INFORMATION: /product= "OTHER"
             /label= Xaa
             /note= "d-serine"

(ix) FEATURE:
         (A) NAME/KEY: Modified-site
         (B) LOCATION: 8
         (D) OTHER INFORMATION: /product= "OTHER"
             /label= Xaa
             /note= "1-napthylalanine"

(xi) SEQUENCE DESCRIPTION: SEQ ID NO:10:

Leu Cys Phe Xaa Cys Tyr Leu Xaa Tyr Thr
1               5                   10

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 4
         (D) OTHER INFORMATION: /product= "OTHER"
             /label= Xaa
             /note= "d-serine"

(xi) SEQUENCE DESCRIPTION: SEQ ID NO:11:

Leu Asn Phe Xaa Cys Tyr Leu Trp Cys Thr
1               5                   10
```